US010610095B2

(12) United States Patent
Franke et al.

(10) Patent No.: US 10,610,095 B2
(45) Date of Patent: Apr. 7, 2020

(54) APPARATUS AND METHOD FOR DRY EYE FORECAST AND TREATMENT RECOMMENDATION

(71) Applicant: Oculeve, Inc., South San Francisco, CA (US)

(72) Inventors: Manfred Franke, Valencia, CA (US); Chao Liu, San Francisco, CA (US); Abirami Muralidharan, Valencia, CA (US); James Donald Loudin, Alhambra, CA (US); Douglas Michael Ackermann, Reno, NV (US); Michael G. Rogers, Menlo Park, CA (US)

(73) Assignee: Oculeve, Inc., Madison, NJ (US)

( * ) Notice: Subject to any disclaimer, the term of this patent is extended or adjusted under 35 U.S.C. 154(b) by 212 days.

(21) Appl. No.: 15/827,683

(22) Filed: Nov. 30, 2017

(65) Prior Publication Data

US 2018/0153394 A1    Jun. 7, 2018

Related U.S. Application Data

(60) Provisional application No. 62/469,440, filed on Mar. 9, 2017, provisional application No. 62/429,694, filed on Dec. 2, 2016.

(51) Int. Cl.
*A61B 3/10* (2006.01)
*G16H 20/00* (2018.01)
(Continued)

(52) U.S. Cl.
CPC ............ *A61B 3/101* (2013.01); *A61B 3/0025* (2013.01); *G06F 19/3418* (2013.01);
(Continued)

(58) Field of Classification Search
CPC ..... A61B 3/101; A61B 3/0025; A61B 3/0033; A61B 5/6802; A61B 5/742; G16H 50/20;
(Continued)

(56) References Cited

U.S. PATENT DOCUMENTS 2,512,882 A    6/1950  Truesdale
2,525,381 A    10/1950 Tower
(Continued)

FOREIGN PATENT DOCUMENTS

CN      1488331 A      4/2004
CN    101087822 A    12/2007
(Continued)

OTHER PUBLICATIONS

Friedman (2010) "Impact of Dry Eye Disease and Impact on Quality of Life", Current Opinion in Ophthalmology, 21:310-316.
(Continued)

*Primary Examiner* — Collin X Beatty
(74) *Attorney, Agent, or Firm* — Mintz Levin Cohn Ferris Glovsky and Popeo, P.C.

(57) ABSTRACT

Generally, a machine may include a processor and a memory connected to the processor, where the memory stores instructions executed by the processor to determine first and second properties related to dry eye symptoms of a patient. The properties may be used to form a dry eye forecast. A treatment recommendation may be selected based at least in part upon the dry eye forecast. The treatment recommendation may be supplied to a device.

44 Claims, 6 Drawing Sheets

(51) Int. Cl.
*G16H 50/20* (2018.01)
*A61B 3/00* (2006.01)
*G06F 19/00* (2018.01)
*G16H 15/00* (2018.01)
*A61B 5/00* (2006.01)
*A61K 9/00* (2006.01)

(52) U.S. Cl.
CPC .............. *G16H 20/00* (2018.01); *G16H 50/20* (2018.01); *A61B 3/0033* (2013.01); *A61B 5/6802* (2013.01); *A61B 5/742* (2013.01); *A61K 9/0048* (2013.01); *G16H 15/00* (2018.01)

(58) Field of Classification Search
CPC ...... G16H 20/00; G16H 15/00; A61K 9/0048; G06F 19/3418
See application file for complete search history.

(56) References Cited

U.S. PATENT DOCUMENTS

| | | |
|---|---|---|
| 3,620,219 A | 11/1971 | Barker |
| 3,709,228 A | 1/1973 | Barker et al. |
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,352,445 A | 10/1994 | Lavaux |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,935,155 A | 8/1999 | Humayun et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,200,626 B1 | 3/2001 | Grobe, III et al. |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,389 B1 | 3/2008 | Newsome |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |

(56) References Cited

U.S. PATENT DOCUMENTS

| | | |
|---|---|---|
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,079 B2 | 2/2011 | Tu |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,083,787 B2 | 12/2011 | Korb et al. |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,521,292 B2 | 8/2013 | Wei et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 9,956,397 B2 | 5/2018 | Loudin et al. |
| D826,420 S | 8/2018 | Ackermann et al. |
| 10,143,846 B2 | 12/2018 | Ackermann et al. |
| D837,396 S | 1/2019 | Ackermann et al. |
| 10,207,108 B2 | 2/2019 | Franke et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0014089 A1 | 1/2003 | Chow et al. |
| 2003/0045909 A1 | 3/2003 | Gross et al. |
| 2003/0045911 A1 | 3/2003 | Bruchmann et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0133877 A1 | 7/2003 | Levin |
| 2003/0176892 A1 | 9/2003 | Shalev |
| 2003/0176898 A1 | 9/2003 | Gross et al. |
| 2003/0192784 A1 | 10/2003 | Zhou et al. |
| 2003/0229381 A1 | 12/2003 | Hochmair et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0004625 A1 | 1/2005 | Chow |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0256570 A1 | 11/2005 | Azar |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0206162 A1 | 9/2006 | Wahlstrand et al. |
| 2006/0216317 A1 | 9/2006 | Reinhard et al. |
| 2006/0235430 A1 | 10/2006 | Le et al. |
| 2006/0239482 A1 | 10/2006 | Hatoum et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2006/0276738 A1 | 12/2006 | Becker |
| 2007/0031341 A1 | 2/2007 | DiMauro et al. |
| 2007/0038250 A1 | 2/2007 | He et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299420 A1 | 12/2007 | Peyman |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109054 A1 | 5/2008 | Hastings et al. |
| 2008/0114424 A1 | 5/2008 | Grenon et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208287 A1 | 8/2008 | Palermo et al. |
| 2008/0208335 A1 | 8/2008 | Blum et al. |
| 2008/0221642 A1 | 9/2008 | Humayun et al. |
| 2008/0269648 A1 | 10/2008 | Bock |
| 2008/0288036 A1 | 11/2008 | Greenberg et al. |

(56) References Cited

U.S. PATENT DOCUMENTS

| | | |
|---|---|---|
| 2008/0294066 A1 | 11/2008 | Hetling et al. |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | Demaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2009/0312818 A1 | 12/2009 | Horsager et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0100165 A1 | 4/2010 | Swanson et al. |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0311688 A1* | 12/2010 | Chapin ................ A61K 9/0048 514/57 |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan et al. |
| 2011/0076775 A1 | 3/2011 | Stewart et al. |
| 2011/0077551 A1 | 3/2011 | Videbaek |
| 2011/0077698 A1 | 3/2011 | Tsampazis et al. |
| 2011/0081333 A1 | 4/2011 | Shantha et al. |
| 2011/0082518 A1 | 4/2011 | Filippello |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0270067 A1 | 11/2011 | Faraji et al. |
| 2011/0270348 A1 | 11/2011 | Goetz |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2011/0313488 A1 | 12/2011 | Hincapie Ordonez et al. |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0072755 A1 | 3/2013 | Papania et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1 | 10/2013 | Otto et al. |
| 2013/0304154 A1 | 11/2013 | Goodman et al. |
| 2013/0310887 A1 | 11/2013 | Curtis |
| 2013/0336557 A1 | 12/2013 | Cruzat et al. |
| 2014/0012182 A1 | 1/2014 | Shantha et al. |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0156000 A1 | 6/2014 | Campin et al. |
| 2014/0163580 A1 | 6/2014 | Tischendorf et al. |
| 2014/0214115 A1 | 7/2014 | Greiner et al. |
| 2014/0214118 A1 | 7/2014 | Greiner et al. |
| 2014/0214120 A1 | 7/2014 | Simon et al. |
| 2014/0214124 A1 | 7/2014 | Greiner et al. |
| 2014/0214125 A1 | 7/2014 | Greiner et al. |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2015/0362755 A1 | 12/2015 | Lee et al. |
| 2016/0022992 A1 | 1/2016 | Franke et al. |
| 2016/0058615 A1 | 3/2016 | Camras et al. |
| 2016/0080720 A1 | 3/2016 | Fullam |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |
| 2017/0188947 A1* | 7/2017 | Connor ................ A61B 5/6803 |
| 2017/0239459 A1 | 8/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368333 A1 | 12/2017 | Loudin et al. |
| 2017/0368359 A1 | 12/2017 | Loudin et al. |

(56) References Cited

U.S. PATENT DOCUMENTS

| | | | |
|---|---|---|---|
| 2018/0064940 | A1 | 3/2018 | Ackermann et al. |
| 2018/0064941 | A1 | 3/2018 | Ackermann et al. |
| 2018/0064942 | A1 | 3/2018 | Ackermann et al. |
| 2018/0154137 | A1 | 6/2018 | Ackermann et al. |
| 2018/0154161 | A1 | 6/2018 | Ackermann et al. |
| 2018/0161579 | A1 | 6/2018 | Franke et al. |
| 2018/0280688 | A1 | 10/2018 | Loudin et al. |
| 2019/0022392 | A1 | 1/2019 | Franke et al. |
| 2019/0167978 | A1 | 6/2019 | Ackermann et al. |
| 2019/0217095 | A1 | 7/2019 | Franke et al. |
| 2019/0282804 | A1 | 9/2019 | Ackermann et al. |
| 2019/0290922 | A1 | 9/2019 | Ackermann et al. |
| 2019/0308009 | A1 | 10/2019 | Loudin et al. |
| 2019/0344077 | A1 | 11/2019 | Ackermann et al. |

FOREIGN PATENT DOCUMENTS

| | | |
|---|---|---|
| CN | 101503491 A | 8/2009 |
| CN | 101589085 A | 11/2009 |
| CN | 101939043 A | 1/2011 |
| CN | 102266592 A | 12/2011 |
| CN | 103467652 A | 12/2013 |
| DE | 102006048819 A | 4/2008 |
| EM | 2102681-0001 | 10/2012 |
| EM | 2199000-0001 | 3/2013 |
| EP | 0 109 935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| EP | 3263175 A1 | 1/2018 |
| GB | 2 129 690 B | 3/1987 |
| GB | 2 456 002 A | 7/2009 |
| JP | S60500241 A | 2/1985 |
| JP | 2002-519138 A | 7/2002 |
| JP | 2002-325851 A | 11/2002 |
| JP | 2002-539859 A | 11/2002 |
| JP | 2004-508847 A | 3/2004 |
| JP | 2004-526510 A | 9/2004 |
| JP | 2005-502409 A | 1/2005 |
| JP | 2005-052461 A | 3/2005 |
| JP | 2005-144178 A | 6/2005 |
| JP | 2005-521489 A | 7/2005 |
| JP | 2005-528169 A | 9/2005 |
| JP | 2006-515900 A | 6/2006 |
| JP | 2006-311917 A | 11/2006 |
| JP | 2007-044323 A | 2/2007 |
| JP | 2007-528751 A | 10/2007 |
| JP | 2008-55000 A | 3/2008 |
| JP | 2008-183248 A | 8/2008 |
| JP | 2008-541850 A | 11/2008 |
| JP | 2009-506836 A | 2/2009 |
| JP | 2009-523503 A | 6/2009 |
| JP | 2010-505563 A | 2/2010 |
| JP | 2010-051562 A | 3/2010 |
| JP | 2010-506654 A | 3/2010 |
| JP | 2010-537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| JP | 2012-200558 A | 10/2012 |
| JP | 2013-528416 A | 7/2013 |
| RU | 2338492 C1 | 11/2008 |
| WO | WO-00/01320 A2 | 1/2000 |
| WO | WO-00/56393 A1 | 9/2000 |
| WO | WO-00/62672 A1 | 10/2000 |
| WO | WO-01/85094 A2 | 11/2001 |
| WO | WO-02/078592 A2 | 10/2002 |
| WO | WO-03/023907 A1 | 3/2003 |
| WO | WO-03/082080 A2 | 10/2003 |
| WO | WO-2003/087433 A1 | 10/2003 |
| WO | WO-03/101535 A1 | 12/2003 |
| WO | WO-2004/026106 A2 | 4/2004 |
| WO | WO-2004/043214 A3 | 5/2004 |
| WO | WO-2004/043217 A2 | 5/2004 |
| WO | WO-2004/026106 A3 | 7/2004 |
| WO | WO-2004/091453 A1 | 10/2004 |
| WO | WO-2004/112893 A2 | 12/2004 |
| WO | WO-2005/007234 A2 | 1/2005 |
| WO | WO-2005/007234 A3 | 1/2005 |
| WO | WO-2004/112893 A3 | 4/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/028003 A2 | 3/2007 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/162793 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/153218 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |

OTHER PUBLICATIONS

McDonald et al. (2009) "Hydroxypropyl Cellulose Ophthalmic Inserts (Lacrisert) Reduce the Signs and Symptoms of Dry Eye Syndrome and Improve Patient Quality of Life", Transactions of the American Ophthalmological Society, 107:214-222.

Olsen et al. (1998) "Human Sclera: Thickness and Surface Area." American Journal of Ophthalmology. Feb. 1998, vol. 125, Issue 2, pp. 237-241.

Yu et al. (Apr. 2011) "The Economic Burden of Dry Eye Disease in the United States: a Decision Tree Analysis", Cornea, 30(4):379-387.

Acar, M. et al. (2013). "Ocular surface assessment in patients with obstructive sleep apnea-hypopnea syndrome," Sleep Breath 17(2):583-588.

Amparo (2013). "Topical Interleukin 1 Receptor Antagonist for Treatment of Dry Eye Disease," JAMA Ophth. 131(6):E1-E9.

Anonymous (2007). "The epidemiology of dry eye disease: report of the Epidemiology Subcommittee of the International Dry Eye WorkShop (2007)," Ocul. Surf. 5(2):93-107.

Bajpai et al. (2012). "Preparation, Characterization and Water Uptake Behavior of Polysaccharide Based Nanoparticles," Prog. Nanotech. Nanomat. 1(1):9-17.

(56) References Cited

OTHER PUBLICATIONS

Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.
Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009;123;1342-1348.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth. 45(2):S227-S239.
Cipriano et al. (2014). "Superabsorbent Hydrogels That are Robust and Highly Stretchable," Am. Chem Soc. 47(13):4445-4452.
Corrected Notice of Allowance dated Feb. 23, 2015, for U.S. Appl. No. 14/256,915, filed Apr. 18, 2014, 2 pages.
Corrected Notice of Allowance dated Jun. 9, 2017, for U.S. Appl. No. 14/920,860, filed Oct. 22, 2015, 2 pages.
Corrected Notice of Allowance dated Jul. 17, 2017, for U.S. Appl. No. 15/256,392, filed Sep. 2, 2016, 2 pages.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nery Syst 1995;51:109-16.
Elsby et al. (1967). "Lacrimal Secretion in the Cat," Br. J. Pharm. Chemother. 29(1):1-7.
Extended European Search Report dated Nov. 18, 2016, for EP Application No. 14 785 631.4, filed on Apr. 18, 2014, 7 pages.
Extended European Search Report dated Sep. 19, 2017, for EP Application No. 15 754 827.2, filed on Feb. 24, 2015, 9 pages.
Extended European Search Report dated Jan. 8, 2018, for EP Application No. 15 824 539.9, filed on Jul. 24, 2015, 6 pages.
Eye Health (2014). "Watery eyes in cold weather," Oregon Eye Specialists, PC, located at http://www.oregoneyes.net/watery-eyes-in-cold-weather/, 3 total pages.
Final Office Action for U.S. Appl. No. 14/256,916, dated Apr. 8, 2015, 16 pages.
Final Office Action for U.S. Appl. No. 14/313,937 dated Apr. 29, 2015, 13 pages.
Final Office Action for U.S. Appl. No. 14/630,471, dated Sep. 26, 2016, 22 pages.
Final Office Action for U.S. Appl. No. 14/256,916, dated Aug. 19, 2016, 19 pages.
Final Office Action dated Sep. 23, 2016, for U.S. Appl. No. 14/809,109, filed Jul. 24, 2015, 10 pages.
Final Office Action dated Feb. 1, 2017, for U.S. Appl. No. 14/920,852, filed Oct. 22, 2015, 20 pages.
Final Office Action dated Nov. 8, 2017, for U.S. Appl. No. 14/256,916, filed Apr. 18, 2014, 21 pages.
Final Office Action dated Dec. 20, 2017, for U.S. Appl. No. 14/920,852, filed Oct. 22, 2015, 18 pages.
Final Office Action dated Feb. 22, 2018, for U.S. Appl. No. 14/256,916, filed Apr. 18, 2014, 24 pages.
Final Office Action dated Mar. 28, 2018, for U.S. Appl. No. 15/598,063, filed May 17, 2017, 9 pages.
Friedman et al. (2016). "A nonrandomized, open-label study to evaluate the effect of nasal stimulation on tear production in subjects with dry eye disease," Clin. Ophthal. 10:795-804.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Galor, A. et al. (2014). "Environmental factors affect the risk of dry eye syndrome in a United States veteran population," Opth. 121:972-973.

Gupta et al. (1997). "Nasolacrimal Stimulation of Aqueous Tear Production," Cornea 16(6):645-648.
Harvard Health Publishing (2010). "Dry eyes and what you can try," Harvard Medical School, 2 total pages.
Heigle TJ, Pflugfelder SC. Aqueous tear production in patients with neurotrophic keratitis. Cornea 1996;15:135-8.
Holzer P. Capsaicin: cellular targets, mechanisms of action, and selectivity for thin sensory neurons. Pharmacol Rev 1991;43:143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dent. Mat. J. 27:765-774.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report dated Feb. 10, 2016, for PCT Patent Application No. PCT/US2015/57021, filed on Oct. 22, 2015, 4 pages.
International Search Report dated Aug. 7, 2017, for PCT Patent Application No. PCT/US2017/30617, filed on May 2, 2017, 2 pages.
International Search Report dated Feb. 12, 2018, for PCT Patent Application No. PCT/US2017/63916, filed on Nov. 30, 2017, 3 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S. Appl. No. 14/313,937, dated Oct. 6, 2015, 7 pages.
Non-Final Office Action Received for U.S. Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Non-Final Office Action dated Jul. 17, 2017, for U.S. Appl. No. 15/598,063, filed May 17, 2017, 9 pages.
Non-Final Office Action dated Jul. 31, 2017, for U.S. Appl. No. 14/920,852, filed Oct. 22, 2015, 18 pages.
Non-Final Office Action dated Dec. 28, 2017, for U.S. Appl. No. 15/676,910, filed Aug. 14, 2017, 10 pages.

(56) References Cited

OTHER PUBLICATIONS

Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Notice of Allowance dated May 26, 2017, for U.S. Appl. No. 14/630,471, filed Feb. 24, 2015, 5 pages.
Notice of Allowance dated Jan. 29, 2018, for U.S. Appl. No. 15/700,935, filed Sep. 11, 2017, 7 pages.
Notice of Allowance dated Feb. 13, 2018, for U.S. Appl. No. 15/700,935, filed Sep. 11, 2017, 2 pages.
Pasqui et al. (2012). "Polysaccharide-Based Hydrogels: The Key Role of Water in Affecting Mechanical Properties," Polymers 4(3):1517-1534.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Vapor Pressure Data for H2O (2012). Handbook of Chemistry and Physics, 73rd edition, 1 total page.
Van Setten, G. et al. (2016). "Evidence of seasonality and effects of psychrometry in dry eye disease," Acta Opth. 94:499-506.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016, 5 pages.
Written Opinion of the International Search Authority dated Aug. 7, 2017, for PCT Patent Application No. PCT/US2017/30617, filed on May 2, 2017, 4 pages.
Written Opinion of the International Searching Authority dated Feb. 12, 2018, for PCT Patent Application No. PCT/US2017/63916, filed on Nov. 30, 2017, 6 pages.
Zilstorff-Pedersen (1965). "Quantitative Measurements of the Nasolacrimal Reflex," Arch. Oto. 81:457-462.
Non-Final Office Action dated Apr. 2, 2018, for U.S. Appl. No. 15/438,577, filed Feb. 21, 2017, 6 pages.
Ahmed, E. M. et al. (2013, e-published Jul. 18, 2013). "Hydrogel: Preparation, characterization, and applications: A review," Cairo University, Journal of Advanced Research (2015) 6, 105-121.

\* cited by examiner

APPARATUS AND METHOD FOR DRY EYE FORECAST AND TREATMENT RECOMMENDATION

CROSS-REFERENCE TO RELATED APPLICATIONS

This application claims priority to U.S. Provisional Patent Application No. 62/429,694 filed Dec. 2, 2016, and U.S. Provisional Patent Application No. 62/469,440 filed Mar. 9, 2017. Each of these applications is hereby incorporated in its entirety by this reference.

FIELD

This invention relates generally to treatment of dry eye. More particularly, this invention relates to forming a dry eye forecast. The dry eye forecast may be based on properties related to dry eye symptoms. A treatment recommendation may be selected based on the dry eye forecast. Treatment may be applied according to the treatment recommendation.

BACKGROUND

Dry Eye Disease ("DED") is a condition that affects millions of people worldwide. More than 40 million people in North America have some form of dry eye, and many millions more suffer worldwide. DED results from the disruption of the natural tear film on the surface of the eye, and can result in ocular discomfort, visual disturbance, and a reduction in vision-related quality of life. Activities of daily living such as driving, computer use, housework, and reading have also been shown to be negatively impacted by DED. Patients with severe cases of DED are at risk for serious ocular health deficiencies such as corneal ulceration, and can experience a quality of life deficiency comparable to that of moderate-severe angina.

DED is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: 1) insufficient aqueous tear production from the lacrimal glands (e.g. secondary to post-menopausal hormonal deficiency, auto-immune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

Commonly assigned U.S. patent application Ser. No. 14/256,915, filed Apr. 18, 2014, and titled "NASAL STIMULATION DEVICES AND METHODS," U.S. patent application Ser. No. 14/630,471, filed Feb. 24, 2015, and titled "POLYMER FORMULATIONS FOR NASOLACRIMAL STIMULATION," U.S. patent application Ser. No. 14/809,109, filed Jul. 24, 2015, and titled "STIMULATION PATTERNS FOR TREATING DRY EYE," and U.S. patent application Ser. No. 14/920,860, filed Oct. 22, 2015, and titled "STIMULATION DEVICES AND METHODS FOR TREATING DRY EYE," each of which is hereby incorporated by reference in its entirety, describe devices and methods for application of electrical stimulation to sensory neurons in the nasal cavity to activate the nasolacrimal reflex and thereby increase tear production. However, it would be desirable to additionally supply a patient with a treatment recommendation for stimulus delivery.

SUMMARY

Generally, a machine may include a processor and a memory connected to the processor, where the memory stores instructions executed by the processor to determine first and second properties related to dry eye symptoms of a patient. The properties may be used to form a dry eye forecast. A treatment recommendation may be selected based at least in part upon the dry eye forecast. The treatment recommendation may be supplied to a device. In some variations, the machine may further include instructions executed by the processor to determine a third property related to dry eye symptoms of the patient, wherein the instructions to form the dry eye forecast utilize the first, second, and third properties. In some variations, the machine may include instructions executed by the processor to supply the treatment recommendation to the device implemented as a computer device. In some variations, the machine may include instructions executed by the processor to supply the treatment recommendation to the device implemented as a stimulation device.

The properties related to dry eye symptoms may include one or more of an environmental property proximate to the patient or a patient-specific property. For example, a property may be a humidity, a relative humidity, an ambient temperature, a wind speed, a pollution level, a pollen count, condensation data, an air pressure, a vapor pressure, a UV index, a wind chill, a schedule of a patient, or a medical condition of a patient. In one non-limiting example, a first property is a relative humidity (RH) proximate to the patient, a second property is an ambient temperature (T) proximate to the patient, and the dry eye forecast is a value equal to $$\begin{cases} 0, & RH*P(T) > 6.28 \\ 100*[6.28 - RH*P(T)]/6.28, & RH*P(T) \le 6.28 \end{cases}$$

where P(T) is the saturated water vapor pressure at temperature T. In another non-limiting example, the first property is a relative humidity (RH) proximate to the patient, the second property is an ambient temperature (T) proximate to the patient, and the dry eye forecast is a value equal to $$\begin{cases} 0, & RH*P(T) < 3.768 \\ \dfrac{(100*[6.28 - RH*P(T)]/6.28) - 40}{60}*100, & RH*P(T) \ge 3.768 \end{cases}$$

where P(T) is the saturated water vapor pressure at temperature T.

The treatment recommendation may include stimulus delivery to a patient. The stimulus delivery may be an electrical stimulus delivery. The stimulus delivery may include delivery to a nasal mucosa of the patient. The treatment recommendation may specify characteristics of the stimulus delivery, such as a duration of stimulus delivery, a time of stimulus delivery, or a number of periods of stimulus delivery.

DETAILED DESCRIPTION

Described herein are systems and methods for selecting and supplying a treatment recommendation for dry eye. The treatment recommendation may be based on a dry eye forecast representing past, present, or future expected severity of dry eye symptoms of a patient. The dry eye forecast may be based on, for example, environmental properties proximate to a patient or patient-specific properties, such as a patient's schedule or medical history. The treatment recommendation may be selected to reduce current dry eye symptoms and/or prevent future dry eye symptoms. As such, supplying such a treatment recommendation may allow for reduction in symptoms using a minimum amount of treatment, may allow treatment to be tailored for a particular patient and/or environment, and/or may allow a patient to avoid or reduce future symptoms by administering prophylactic treatment. The recommended treatment may include stimulus delivery (e.g., electrical stimulus delivery) to the patient (e.g., to nasal mucosa of the patient). The treatment recommendation may specify characteristics of the stimulus delivery, such as the timing for stimulus delivery, duration of stimulus delivery, and/or parameters of stimulus delivery (e.g., waveform of an electrical stimulus).

Systems

In general, the systems described herein may comprise a stimulation device and a patient device comprising a treatment recommendation application. The systems may further comprise a server, which may comprise a dry eye forecast module and a treatment selection module, and a database server, which may comprise an environmental property database and a patient-specific property database. Some or all of the stimulation device, patient device, server, and database server may communicate via a network.

Figure 1:
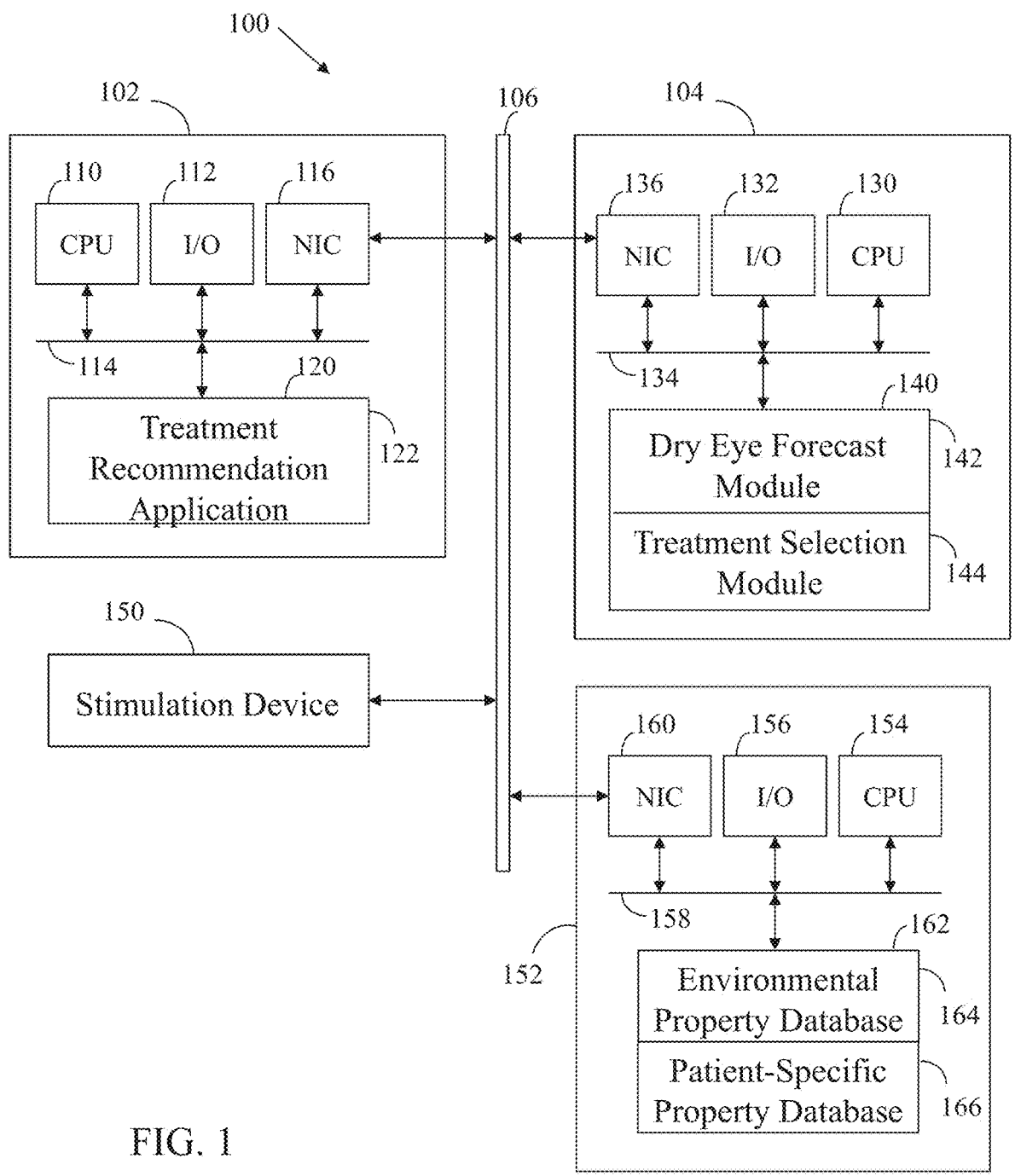
FIG. 1 illustrates a system configured in accordance with an embodiment of the invention.

As one example, FIG. 1 illustrates a system 100 configured in accordance with an embodiment of the invention. The system 100 includes a stimulation device 150 and a patient device 102 that communicates with a server 104 via a network 106, which may be any combination of wired and/or wireless networks. The system 100 also includes a database server 152 that communicates with the server 104 via the network 106.

Patient Device

In an exemplary variation, the patient device 102 includes a central processing unit 110 linked to input/output devices 112 via a bus 114. The input/output devices 112 may include a keyboard, mouse, touch display, and the like. A network interface circuit 116 may also be connected to the bus 114. The network interface circuit 116 may provide connectivity to network 106. A memory 120 may also be connected to the bus 114. The memory 120 may store a treatment recommendation application 122 with instructions executed by the central processing unit 110 to implement operations disclosed herein. In some variations, the memory 120 may also store patient-specific properties related to dry eye symptoms, such as a schedule of a patient or a medical condition of a patient. The patient device 102 may be a computer, tablet, smart phone, and the like.

In some variations, the patient device 102 may comprise one or more sensors for determining a property, such as an environmental property proximate to the sensor. For example, the patient device 102 may comprise a temperature sensor, humidity sensor, wind sensor, and/or air pressure sensor. In some variations, a sensor (e.g., temperature sensor, humidity sensor, wind sensor, air pressure sensor) may be located in a separate device (i.e., separate from the patient device), such as but not limited to a keychain dongle, belt clip, or other wearable device, that is connected to the network 106. In some variations, a sensor may be located in a stimulation device such as the stimulation device 300 described with respect to FIG. 3. In some variations, the sensor may be located in a base unit configured for charging and/or sending/retrieving data from a stimulation device, where the base unit is connected to the network 106.

Server

Server 104 may also include components including a central processing unit 130, input/output devices 132, a bus 134, and a network interface circuit 136. A memory 140 may be connected to the bus 134. The memory 140 may store instructions executed by the central processing unit 130 to implement operations disclosed herein. In one embodiment, the memory stores a dry eye forecast module 142. The dry eye forecast module determines properties related to dry eye symptoms of a patient and uses them to form a dry eye forecast for the patient. The memory 140 also may also store a treatment selection module 144. The treatment selection module 144 selects a treatment recommendation based upon the dry eye forecast. It should be appreciated that modules 142 and 144 may be incorporated into the treatment recommendation application 122. In such a variation, all processing may be performed by the patient device 102 without communicating with server 104.

Database Server

The database server 152 may also include components including a central processing unit 154, input/output devices 156, a bus 158, and a network interface circuit 160. A memory 162 may store an environmental property database 164 and a patient-specific property database 166.

The environmental property database 164 may contain one or more environmental properties related to dry eye symptoms. For example, the property may be a humidity or relative humidity, an ambient temperature, a wind speed, a pollution level, a pollen count, condensation data, an air pressure, a vapor pressure, a UV index, and/or a wind chill. When the property is an environmental property, the environmental property may be associated with a location proximate to the patient. The environmental property may also be associated with a time. For example, the environmental property may be associated with a current time, a past time, or a future time.

The patient-specific property database 166 may contain one or more patient-specific properties related to dry eye symptoms. For example, the property may be a schedule of a patient, a medical condition of a patient, a treatment history of a patient, or a reported symptom severity of a patient. It should be appreciated that in other variations, patient-specific properties may additionally or alternatively be stored by the memory 120 of patient device 102. It should also be appreciated that in these or other variations, the environmental property database and patient-specific property database may be on different database servers, each containing a central processing unit, input/output devices, a bus, a network interface circuit, and a memory.

Methods

The methods described herein may comprise forming a dry eye forecast from one or more properties related to dry eye symptoms of a patient, and using the dry eye forecast to select a treatment recommendation. The treatment recommendation may be supplied and used to provide treatment (e.g., stimulus delivery) to a patient.

Determine First Property

Figure 2:
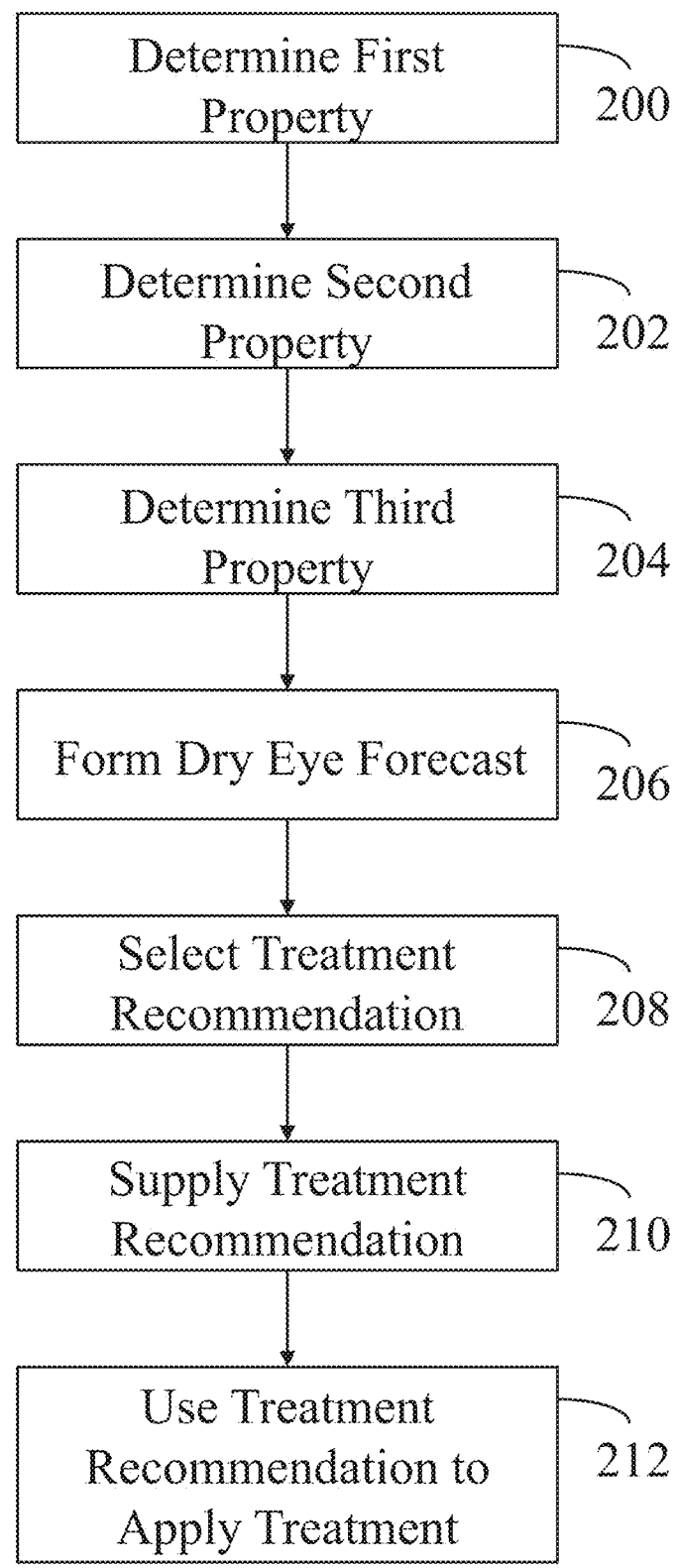
FIG. 2 illustrates a method performed in accordance with an embodiment of the invention.

FIG. 2 illustrates operations associated with an embodiment of the invention. Initially, a first property is determined 200. The first property may be any of the properties described herein, such as an environmental property or a patient-specific property. The dry eye forecast module 142 may be used to implement this operation. For example, the dry eye forecast module 142 may retrieve one or more properties from the database server 152.

In variations in which the property is an environmental property, the environmental property may be associated with a location proximate to the patient. Accordingly, in some variations the dry eye forecast module 142 may provide a location interface to the patient device 102. The location interface may be displayed by an output device (e.g., a display) 112 associated with the patient device 102. The patient may use the location interface to input a location (e.g., a zip code, a city and state, a point on a displayed map, etc.). In other variations, a location of a patient may be determined using a location application stored by the memory 120 of the patient device 102, such as a global positioning system application. The first property may be retrieved from the environmental property database based on the location. In other variations, the first property may be retrieved from a sensor (e.g., a temperature sensor, humidity sensor, wind sensor, air pressure sensor, etc.) proximate to the patient. For example, the first property may be retrieved from a sensor on the patient device 102, on a separate wearable device, on a stimulation device, or on a base unit for a stimulation device. As one non-limiting example, the environmental property may be a humidity or a relative humidity proximate to the patient.

It should be appreciated that in other variations in which the property is an environmental property, the environmental property may be associated with a location not proximate to the patient at the time of determining the first property. For example, the location may be a location proximate to the patient at a future time, such as, for example, if the patient intends to travel in the future. In some of these variations, the dry eye forecast module 142 may provide a location interface to the patient device 102. The location interface may be displayed by an output device (e.g., a display) 112 associated with the patient device 102. The patient may use the location interface to input a location (e.g., a zip code, a city and state, a point on a displayed map, etc.). The inputted location may, for example, correspond to an intended location of the patient at a future time. In other variations, the location of a patient may be determined using an application stored by the memory 120 of the patient device 102, such as a location stored for a future date in a calendar application.

In variations in which the property is a patient-specific property and a patient-specific property database 166 contains one or more patient-specific properties related to dry eye symptoms, the patient-specific property may be determined from the patient-specific property database 166. In variations in which the property is a patient-specific property and is stored by the memory 120 of the patient device 102, the patient-specific property may be retrieved from the patient device 102. In some variations the dry eye forecast module 142 may provide a patient-specific property interface to the patient device 102. The interface may be displayed by an output device (e.g., a display) 112 associated with the patient device 102. The patient may use the interface to input a patient-specific property. As non-limiting examples, for instance, the patient may use the interface to input a daily schedule or information about current dry eye symptom severity.

Determine Second Property

A second property may be determined 202. The second property may be any of the properties described herein, such as an environmental property or a patient-specific property. The dry eye forecast module 142 may be used to implement this operation. For example, the dry eye forecast module 142 may retrieve one or more properties from the database server 152.

In variations in which the property is an environmental property, the environmental property may be associated with a location proximate to the patient. Accordingly, in some variations the dry eye forecast module 142 may provide to the patient device 102 a location interface. The location interface may be displayed by an output device (e.g., a display) 112 associated with the patient device 102. The patient may use the location interface to input a location (e.g., a zip code, a city and state, a point on a displayed map, etc.). In other variations, a location of a patient may be determined using a location application stored by the memory 120 of the patient device 102, such as a global positioning system application. The second property may be retrieved from the environmental property database based on the location. In yet other variations, the second property may be retrieved from the environmental property database using the location provided with respect to step 200 in which a first property was determined. In other variations, the second property may be retrieved from a sensor (e.g., a temperature sensor, humidity sensor, wind sensor, air pressure sensor, etc.) proximate to the patient. For example, the second property may be retrieved from a sensor on the patient device 102, on a separate wearable device, on a stimulation device, or on a base unit for a stimulation device. As one non-limiting example, the environmental property may be an ambient temperature proximate to the patient.

It should be appreciated that in other variations in which the property is an environmental property, the environmental property may be associated with a location not proximate to the patient at the time of determining the second property. For example, the location may be a location proximate to the patient at a future time, such as, for example, if the patient intends to travel in the future. In some of these variations, the dry eye forecast module 142 may provide a location interface to the patient device 102. The location interface may be displayed by an output device (e.g., a display) 112 associated with the patient device 102. The patient may use the location interface to input a location (e.g., a zip code, a city and state, a point on a displayed map, etc.). The inputted location may, for example, correspond to an intended location of the patient at a future time. In other variations, the location of a patient may be determined using an application stored by the memory 120 of the patient device 102, such as a location stored for a future date in a calendar application.

In variations in which the property is a patient-specific property and a patient-specific property database 166 contains one or more patient-specific properties related to dry eye symptoms, the patient-specific property may be determined from the patient-specific property database 166. In variations in which the property is a patient-specific property and is stored by the memory 120 of the patient device 102, the patient-specific property may be retrieved from the patient device 102. In some variations the dry eye forecast module 142 may provide a patient-specific property interface to the patient device 102. The interface may be displayed by an output device (e.g., a display) 112 associated with the patient device 102. The patient may use the interface to input a patient-specific property. As a non-limiting example, for instance, the patient-specific property may be a medical condition of the patient.

Determine Third Property

A third property may be determined 204. The third property may be any of the properties described herein, such as an environmental property or a patient-specific property. The dry eye forecast module 142 may be used to implement this operation. For example, the dry eye forecast module 142 may retrieve one or more properties from the database server 152.

In variations in which the property is an environmental property, the environmental property may be associated with a location proximate to the patient. Accordingly, in some variations the dry eye forecast module 142 may provide to the patient device 102 a location interface. The location interface may be displayed by an output device (e.g., a display) 112 associated with the patient device 102. The patient may use the location interface to input a location (e.g., a zip code, a city and state, a point on a displayed map, etc.). In other variations, a location of a patient may be determined using a location application stored by the memory 120 of the patient device 102, such as a global positioning system application. The third property may be retrieved from the environmental property database using the location. In yet other variations, the third property may be retrieved from the environmental property database based on the location provided with respect to step 200 in which a first property was determined, or using the location provided with respect to step 202 in which a second property was determined. As non-limiting examples, the environmental property may be a wind speed, a pollution level, a pollen count, condensation data, an air pressure, a vapor pressure, a UV index, or a wind chill proximate to the patient. In other variations, the third property may be retrieved from a sensor (e.g., a temperature sensor, humidity sensor, wind sensor, air pressure sensor, etc.) proximate to the patient. For example, the third property may be retrieved from a sensor on the patient device 102, on a separate wearable device, on a stimulation device, or on a base unit for a stimulation device.

It should be appreciated that in other variations in which the property is an environmental property, the environmental property may be associated with a location not proximate to the patient at the time of determining the third property. For example, the location may be a location proximate to the patient at a future time, such as, for example, if the patient intends to travel in the future. In some of these variations, the dry eye forecast module 142 may provide a location interface to the patient device 102. The location interface may be displayed by an output device (e.g., a display) 112 associated with the patient device 102. The patient may use the location interface to input a location (e.g., a zip code, a city and state, a point on a displayed map, etc.). The inputted location may, for example, correspond to an intended location of the patient at a future time. In other variations, the location of a patient may be determined using an application stored by the memory 120 of the patient device 102, such as a location stored for a future date in a calendar application.

In variations in which the property is a patient-specific property and a patient-specific property database 166 contains one or more patient-specific properties related to dry eye symptoms, the patient-specific property may be determined from the patient-specific property database 166. In variations in which the property is a patient-specific property and is stored by the memory 120 of the patient device 102, the patient-specific property may be retrieved from the patient device 102. In some variations the dry eye forecast module 142 may provide a patient-specific property interface to the patient device 102. The interface may be displayed by an output device (e.g., a display) 112 associated with the patient device 102. The patient may use the interface to input a patient-specific property.

It should be appreciated that any suitable number of properties may be determined as part of the methods described herein. For example, in some variations of the method, a single property may be determined and used to form a dry eye forecast. In other variations, two properties may be determined and used to form a dry eye forecast, or three properties may be determined and used to form a dry eye forecast. In yet other variations, more than three properties may be determined and used to form a dry eye forecast, such as but not limited to four, five, six, or more properties. Each property may be determined in a similar way as described herein with respect to the first, second, and third properties.

Form Dry Eye Forecast

The determined properties may be used to form a dry eye forecast 206. The dry eye forecast module 142 may implement operation 206. The dry eye forecast may be a representation of the expected severity of dry eye symptoms in a patient. In some variations, the dry eye forecast may represent the expected severity of dry eye symptoms at a single time point, i.e., a past, current, or present time. In other variations, the dry eye forecast may represent the expected severity of dry eye symptoms over a period of time, e.g., over a period of hours or days.

The dry eye forecast may be formed based on the determined properties using a suitable operation. For example, in variations in which a determined property is a humidity or relative humidity level, the dry eye forecast may reflect an increased severity of dry eye symptoms associated with a low humidity or relative humidity level. In variations in which a determined property is an irritant level, such as a pollution level or a pollen count, the dry eye forecast may reflect an increased severity of dry eye symptoms associated with a high irritant level. In variations in which a determined property is a wind speed, the dry eye forecast may reflect an increased severity of dry eye symptoms associated with a high wind speed. In variations in which a determined property is a UV index, the dry eye forecast may reflect an increased severity of dry eye symptoms associated with a high UV index. In variations in which a determined property is a schedule of a patient, the dry eye forecast may reflect an increased severity of dry eye symptoms associated with certain activities, such as but not limited to airplane travel, nighttime driving, and computer use. In variations in which a determined property is a medical condition of a patient, the dry eye forecast may reflect an increased severity of dry eye symptoms associated with certain medical conditions, such as but not limited to Sjögren's syndrome. In variations in which a determined property is a treatment history of a patient, the dry eye forecast may reflect an increased severity of dry eye symptoms associated with a history of more extensive treatment for dry eye disease, such as but not limited to more frequent use of intranasal stimulation, longer duration of intranasal stimulation, and use of other therapies for dry eye (e.g., artificial tears, cyclosporine, etc.).

As one example, the dry eye forecast may be based at least partially on the amount of expected tear evaporation. Expected tear evaporation may be calculated using the properties described herein, such as environmental and patient-specific properties, as well as estimates of the surface area of tear in contact with air, and tear temperature. Any suitable method for estimating expected tear evaporation from the determined properties may be used in forming a dry eye forecast. For example, when E is the evaporation rate (Kg/min), P is water's vapor pressure at ambient temperature (kPa), V is the velocity of air above the water surface (m/s), A is the surface area of water (m$^2$), $T_a$ is the ambient temperature (K), M is the molecular weight of water (18.02 g/mol or dimensionless), R is the universal gas constant (8314.5 Pa·m$^3$/(kmol·K)), Ø is the evaporation coefficient (Kg/m$^2$*h), Xs is the humidity ratio in saturated air (Kg Water/Kg of moist air), and X is the humidity ratio in air (Kg Water/Kg of dry air), the evaporation rate may be estimated according to one of the following equations $$\text{evaporation rate} = \left[\frac{0.106 P A M^{2/3} V^{0.78}}{R T_a}\right] \text{ or}$$

$$\text{evaporation rate} = \left[\frac{0.002 V P A M}{R T_a}\right] \text{ or}$$

$$\text{evaporation rate} = \frac{\emptyset A (X_s - X)}{60}, \text{ where}$$

$$X_s = 0.622 * \frac{p_{ws}}{p_a - p_{ws}} \text{ and } p_{ws} = \frac{e^{(77.35 + 0.0057T - 7235/T)}}{T^{8.2}}, \text{ and}$$

$$X = 0.622 * \frac{p_w}{p_a - p_w}$$

where $p_w$ is the partial vapor pressure of water vapor in moist air (Pa) (relative humidity*$p_{ws}$) $p_a$ is the atmospheric pressure of moist air (Pa), $p_{ws}$ is the saturation pressure of water vapor, and T is the temperature (Kelvin). Because $p_w$ is small relative to $p_a$, the relationship between X and Xs is almost linear.

For example, FIGS. 4A-4D show examples of expected tear evaporation when a first property is temperature, a second property is relative humidity, a third property is pressure, and a fourth property is wind speed. These figures show scatterplots of calculated average evaporation rates based on the environmental properties proximate to a patient of temperature, relative humidity, pressure, and wind speed, using the third formula above $$\left(\text{evaporation rate} = \frac{\emptyset A (X_s - X)}{60}\right).$$

Figure 4A:
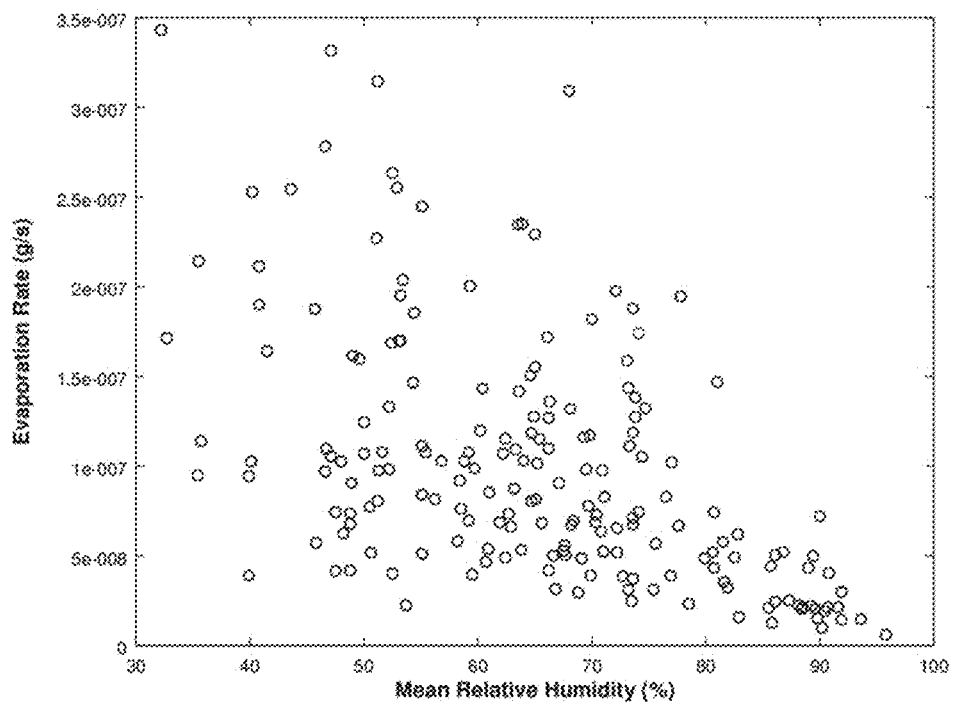
FIGS. 4A-4D are scatterplots of evaporation rate versus relative humidity (FIGS. 4A and 4C) and versus temperature (FIGS. 4B and 4D) for first (FIGS. 4A-4B) and second (FIGS. 4C-4D) geographic locations.
Figure 4B:
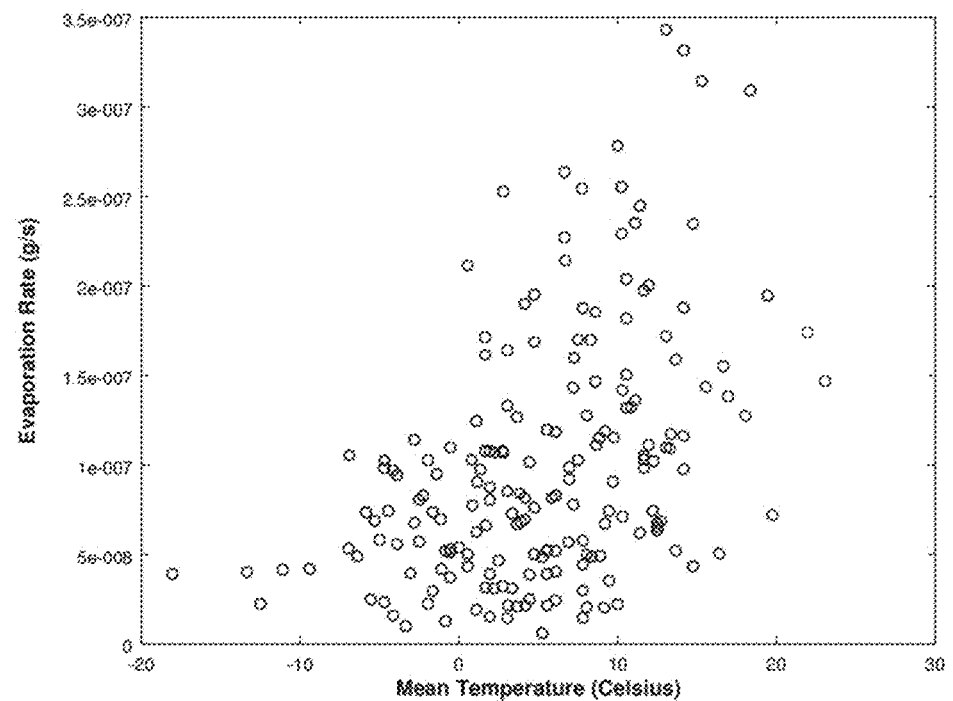
Figure 4C:
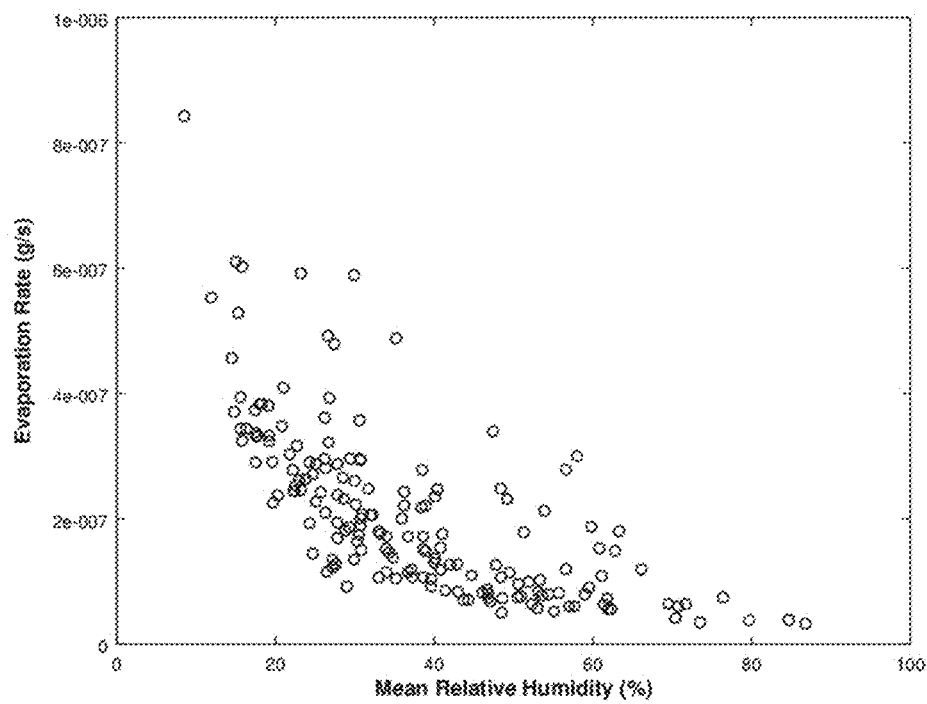
Figure 4D:
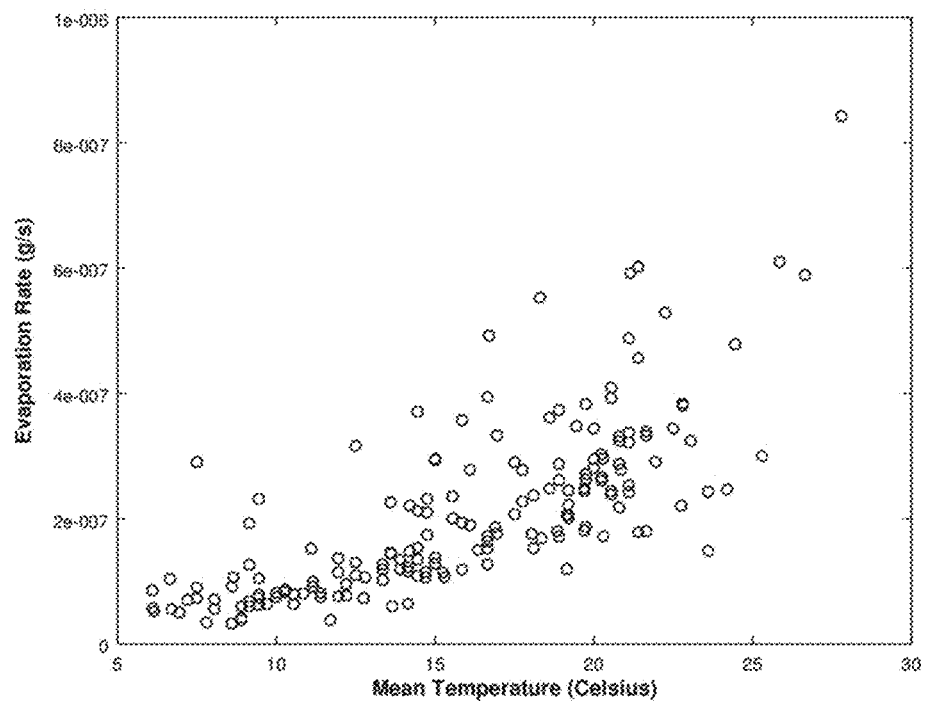

FIGS. 4A-4B are scatterplots of evaporation rate (g/s) versus mean relative humidity (%) (FIG. 4A) and versus mean temperature (Celsius) (FIG. 4B) for a first geographic location. FIGS. 4C-4D are scatterplots of evaporation rate (g/s) versus mean relative humidity (%) (FIG. 4C) and versus mean temperature (Celsius) (FIG. 4D) for a second geographic location. Each data point is for a particular day. The surface area of the tear was assumed to be 2 cm$^2$, and the determined environmental properties (temperature, relative humidity, pressure, and wind speed) were average values for each day. The range of average evaporation rates (g/s) at each location are shown in Table 1 below.

TABLE 1

Range of average evaporation rates (g/s) at two locations.

| Location | Min | Max | Median | 25% | 75% |
|---|---|---|---|---|---|
| First Location | 6.02e−9 | 3.43e−7 | 8.06e−8 | 4.85e−8 | 1.25e−7 |
| Second Location | 3.27e−8 | 8.43e−7 | 2.00e−7 | 1.07e−7 | 2.90e−7 |

The dry eye forecast for each day in each location may be based on the calculated evaporation rate. For example, in some variations the dry eye forecast may be a value equal to or positively correlated with the evaporation rate, with higher values corresponding to more severe dry eye symptoms, and lower values corresponding to less severe dry eye symptoms.

In other variations, expected tear evaporation may be at least partially based on other models using the relationship between water vapor pressure of air proximate to a patient and water vapor pressure of the tear film. For instance, the patient and tear film may be assumed to be a heat sink held at body temperature, which is 37° C. (310.15 Kelvin). The patient's local environment may be assumed to be an independent heat sink, with temperature T and relative humidity RH. Air mixing may be assumed to be instantaneous and complete, so that no layer of warm air is formed above the eye. Based on these assumptions, the water vapor pressure of air (pressure exerted by water molecules arriving at a surface) is equal to air water vapor pressure=$RH*P(T)$ where P(T) is the saturated water vapor pressure at temperature T. Also based on these assumption, the water vapor pressure of a tear (pressure exerted by water molecules exiting the liquid phase and entering the gaseous phase) is equal to tear water vapor pressure=$P(37° C.)$=6.28 kPa.

The difference between the water vapor pressures, δ, of these two heat sinks is thus equal to δ=6.28−$RH*P(T)$ (in kPa).

This differential represents the underlying physical quantity that drives evaporation under these assumptions, and has a maximum of 6.28 kPa (when RH=0%).

Thus, when a first property is a relative humidity (RH) proximate to a patient and a second property is a temperature (T) proximate to the patient, this differential between the water vapor pressures may be used to form a dry eye forecast. For instance, in some variations the invention comprises a dry eye forecast that is a value between 0 (corresponding to the least severe dry eye symptoms) and 100 (corresponding to the most severe dry eye symptoms) derived from dry eye forecast formula (A) below:

$$\text{dry eye forecast value} = \begin{cases} 0, & RH * P(T) > 6.28 \\ 100 * [6.28 - RH * P(T)]/6.28, & RH * P(T) \leq 6.28 \end{cases} \tag{A}$$

where P(T) is the saturated water vapor pressure at temperature T, which may be calculated or looked up in a vapor pressure table. Exemplary dry eye forecast values for various relative humidities and temperatures are shown in Table 2 below.

TABLE 2

Example dry eye forecast values.

| Temperature (° F.) | Humidity (%) | Dry Eye Forecast Value |
|---|---|---|
| 109 | 19 | 74 |
| 107 | 10 | 87 |
| 106 | 21 | 74 |
| 104 | 19 | 78 |
| 103 | 25 | 72 |
| 93 | 62 | 49 |
| 92 | 59 | 53 |
| 92 | 62 | 51 |
| 89 | 70 | 49 |
| 89 | 74 | 46 |
| 78 | 66 | 66 |
| 69 | 54 | 79 |
| 68 | 54 | 80 |
| 67 | 47 | 83 |
| 66 | 46 | 84 |

As another example, if a patient is traveling in an airplane, the relative humidity may be about 20% and the temperature may be about 20° C., resulting in a dry eye forecast value of 92. It should be appreciated that in other variations of the invention, tear evaporation may be modeled using other suitable methods, including methods not assuming perfect air mixing and thus modeling the transition layer. It should also be appreciated that in some variations of the invention, patient feedback regarding dry eye symptom intensity may be used to refine the formation of a dry eye forecast from determined properties. For example, a patient may indicate the severity of his or her dry eye symptoms on a user interface (e.g., on the patient device), where higher ratings of dry eye symptoms contribute to a higher dry eye forecast value (or adjusted dry eye forecast value, described below). In one exemplary variation, the patient may rate the severity of his or her dry eye symptoms on a numerical scale (e.g., 1 to 5, with 1 being not severe and 5 being extremely severe), and the rating may be correlated to a multiplier on the dry eye forecast value obtained via the dry eye forecast formula (A) above (or the adjusted dry eye forecast value formula described below).

In some variations of the invention in which the dry eye forecast is a value, the dry eye forecast may be based on a calculation designed such that the resulting values span a desired range. For example, the dry eye forecast formula (A) above may in theory mathematically result in values between 1 and 100, but real-world, global relative humidity and temperature values may in fact limit the range of resulting dry eye forecast values. In some variations of the invention, a formula for dry eye forecast values may be adjusted such that real-world, global relative humidity and temperature values result in a broader range of resulting dry eye forecast values. As one example, in some variations the invention comprises a dry eye forecast value calculated using the dry eye forecast formula (A) above that is adjusted as follows:

$$\text{adjusted dry eye forecast value} = \frac{\text{value from dry eye forecast formula }(A) - 40}{60} * 100$$

where negative adjusted dry eye forecast values are set to zero. That is, in these variations the invention comprises an adjusted dry eye forecast that is a value between 0 (corresponding to the least severe dry eye symptoms) and 100 (corresponding to the most severe dry eye symptoms) equal to adjusted dry eye forecast value =

$$\begin{cases} 0, & RH*P(T) < 3.768 \\ \frac{(100*[6.28 - RH*P(T)]/6.28) - 40}{60} * 100, & RH*P(T) \geq 3.768 \end{cases}$$

where P(T) is the saturated water vapor pressure at temperature T, which may be calculated or looked up in a vapor pressure table. Example adjusted dry eye forecast values for various relative humidities and temperatures are shown in Table 3 below. As shown there, the values span a broader range (10 to 78) than the unadjusted values of Table 2 (46 to 87).

TABLE 3

Example dry eye forecast values.

| Temperature (° F.) | Humidity (%) | Adjusted Dry Eye Forecast Value |
|---|---|---|
| 109 | 19 | 57 |
| 107 | 10 | 78 |
| 106 | 21 | 57 |
| 104 | 19 | 63 |
| 103 | 25 | 53 |
| 93 | 62 | 15 |
| 92 | 59 | 22 |
| 92 | 62 | 18 |
| 89 | 70 | 15 |
| 89 | 74 | 10 |
| 78 | 66 | 43 |
| 69 | 54 | 65 |
| 68 | 54 | 67 |
| 67 | 47 | 72 |
| 66 | 46 | 73 |

While the example above illustrates an adjustment that is implemented for all dry eye forecast values, in other variations of the invention, dry eye forecast values for one patient may be adjusted differently than dry eye forecast values for another patient. For instance, rather than adjusting all dry eye forecast values in the same way, regardless of a patient's location, dry eye forecast values may be adjusted instead at least partially based on a patient's location. Because certain geographic locations may have particular ranges of environmental properties (e.g., temperatures and humidities), dry eye forecast values based on environmental properties may result in a limited range of values. That is, the range of dry eye forecast values calculated using a universal formula (i.e., the same formula for all geographic locations) based on environmental properties may be limited to a particular range of values within the theoretical range of outputs of the universal formula, and that range may be different for different geographic locations. As another example, when a dry eye forecast is a value based on a patient-specific property such as, for example, a medical condition of the patient, dry eye forecast values for that patient may be limited to a particular range of values due to the medical condition. For example, when the dry eye forecast is a value based on a medical condition of a patient, a patient having Sjögren's syndrome may have dry eye forecast values within a narrow range of severity.

When a patient's dry eye forecast values have variation only within a small range of values, the dry eye forecast values may be less useful for selecting treatment recommendations, and when provided to a patient, less meaningful for the patient. Thus, it may be desirable in some variations to use different formulas for dry eye forecast values (e.g., non-universal formulas) for different patients, such as different formulas for different locations, or different formulas for different medical conditions. In some variations, for example, the invention may comprise carrying out the same initial calculation regardless of location (e.g., using the dry eye forecast formula (A) above), and then applying a location-specific adjustment. In some variations of the invention, for example, such a location-specific adjustment may normalize the distribution of dry eye forecast values for a particular location (e.g., a zip code, a city, etc.) to a uniform distribution within a range (e.g., between 0 and 100). In other variations, for example, the invention may comprise carrying out the same initial calculation regardless of location (e.g., using the dry eye forecast formula (A) above), and then applying a patient-specific adjustment. In some variations of the invention, for example, such a patient-specific adjustment may normalize the distribution of dry eye forecast values for the particular patient to a uniform distribution within a range (e.g., between 0 and 100). The normalization of the distribution of dry eye forecast values may, for example, be based on all previous dry eye forecast values for the patient, or as another example, may be based on a subset of previous dry eye forecast values for the patient, such as but not limited to dry eye forecast values for the patient from the previous week, previous 2 weeks, previous month, previous 3 months, previous 6 months, previous year, or the like.

Once formed, the dry eye forecast may be provided to a patient. For example, the dry eye forecast may be provided to the patient device 102 and displayed by an output device (e.g., a display) 112 associated with the patient device 102. The dry eye forecast may have any suitable form. For example, the dry eye forecast may comprise a single value (e.g., representing the expected severity of dry eye symptoms at a single time point) or a plurality of values (e.g., representing the expected severity of dry eye symptoms over a period of time). When the dry eye forecast is a value or a plurality of values (e.g., between 0 and 100, with 100 representing the most severe symptoms; between 0 and 10, with 10 representing the most severe symptoms; etc.), the value(s) may be displayed by an output device (e.g., a display) 112 as one or more numerals, a line graph, a bar chart, one or more colors, a combination of these forms, or the like.

Figure 5A:
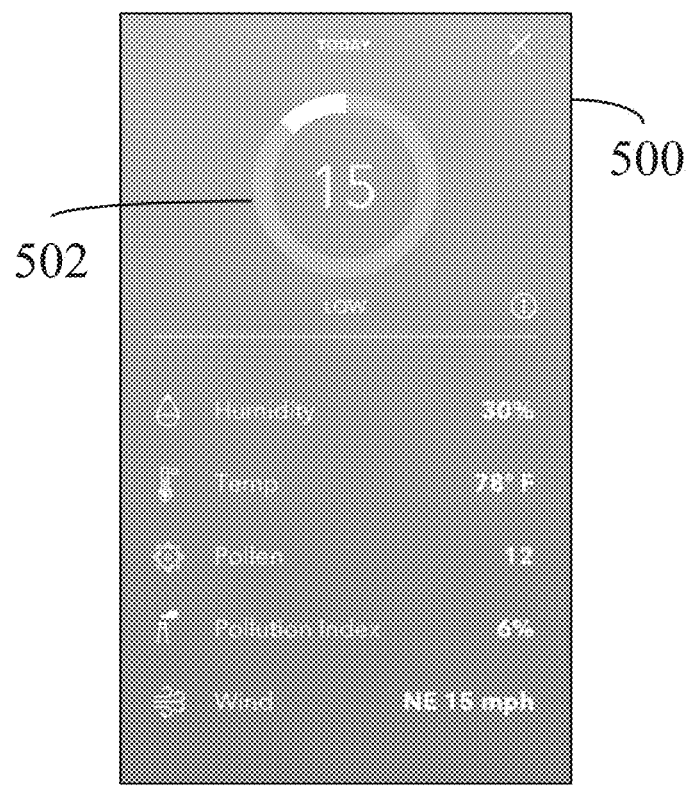
FIGS. 5A-5B show exemplary displays utilized in accordance with an embodiment of the invention.
Figure 5B:
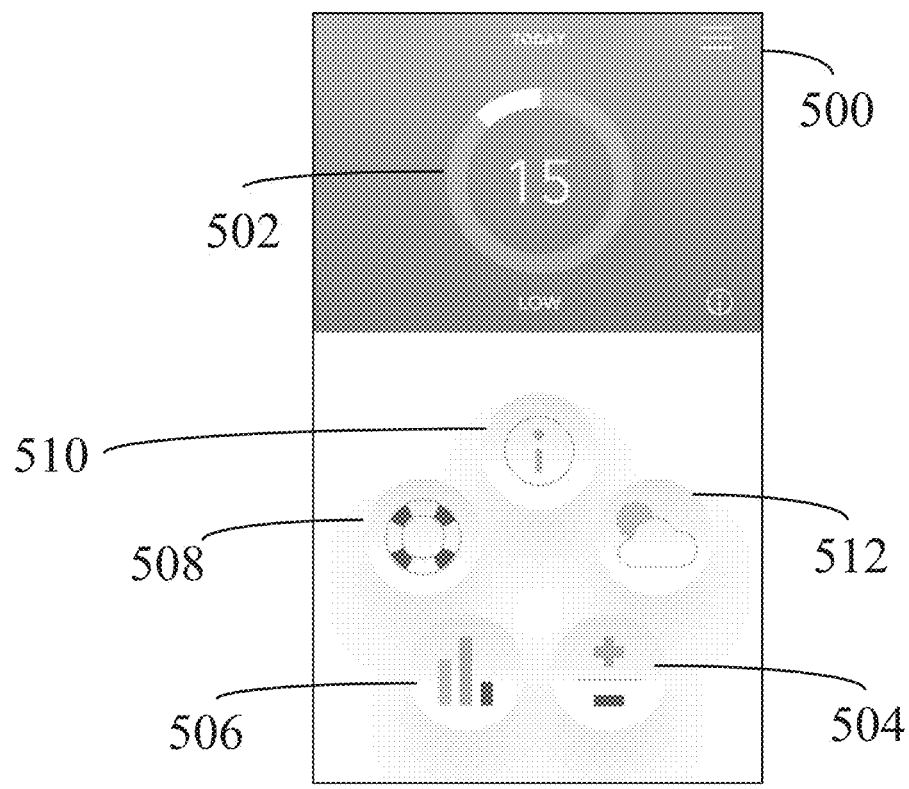

For example, FIGS. 5A-5B show an exemplary display 500 that may be used to provide a dry eye forecast to a patient. In this example, the dry eye forecast is a value and is displayed via an indicator 502 that provides the value numerically, graphically, and/or with text indicating the severity of expected dry eye symptoms (here, "low"). The display 500 may also allow a patient to view properties related to dry eye symptoms, such as humidity, temperature, pollen count, pollution index, and wind, as shown in FIG. 5A. In some variations, the display 500 may present a plurality of dry eye forecasts to a patient, such as the dry eye forecast for a series of days or over a geographic region.

Select Treatment Recommendation

A treatment recommendation may be selected 208 based upon the dry eye forecast. The treatment selection module 144 may implement this operation.

The treatment recommendation may include stimulus delivery to the patient. The treatment recommendation may include various parameters of the stimulus delivery, such as but not limited to one or more of the duration of the stimulus delivery, the time of stimulus delivery, the number of periods of the stimulus delivery, and the form of stimulus delivery (e.g., stimulation waveform). Suitable treatment recommendations are described in commonly assigned U.S. patent application Ser. No. 14/256,915, filed Apr. 18, 2014, U.S. patent application Ser. No. 14/809,109, filed Jul. 24, 2015, and U.S. patent application Ser. No. 14/920,860, filed Oct. 22, 2015, each of which was previously incorporated by reference in its entirety.

The treatment selection based on the dry eye forecast may be intended to achieve one or more goals. For example, in some variations, the treatment recommendation may be selected to prevent worsening of dry eye symptoms; based on the dry eye forecast, the treatment recommendation may include prophylactic stimulus delivery. Additionally or alternatively, the treatment recommendation may be selected to maximize symptom relief with a minimum amount of stimulus delivery, and/or may be selected to optimize the stimulation device battery life. In some variations, the treatment selection module 144 may utilize patient feedback regarding dry eye symptom intensity to refine the algorithm for treatment selection.

Supply Treatment Recommendation

The treatment recommendation may be supplied 210. In some variations, the treatment recommendation may include one or more of a stimulation intensity, stimulation duration, stimulation frequency, and stimulation amplitude. Additionally or alternatively, the treatment recommendation may include a recommendation for frequency of treatment sessions (e.g., every 30 minutes, every hour, etc.).

In the case of a server-based implementation, the treatment recommendation is supplied to the patient device 102 from the server 104 via network 106. In the case of a patient-side implementation, the treatment recommendation application 122 supplies the treatment recommendation to a display on the patient device. FIG. 5B shows the display 500 showing an icon 504 allowing a patient to view and/or supply a treatment recommendation. Also shown are icons 506, 508, 510, and 512, which may allow a patient to view other information, such as but not limited to instructions and support, historical dry eye forecasts, future dry eye forecasts (e.g., a 5-day outlook), data regarding past treatment sessions, and the like.

The treatment recommendation may also be supplied to a stimulation device 150 from either the patient device 102 or the server 104. In these variations, the treatment recommendation may be supplied to the stimulation device 150 either directly or via a base unit.

Use Treatment Recommendation to Apply Treatment

The final operation of FIG. 2 is to use the treatment recommendation to apply treatment 212. In one example, the treatment is electrical stimulation. Stimulation may be carried out manually in accordance with a displayed treatment recommendation. Alternately, stimulation may be automatically executed by the stimulation device 150. Commonly assigned U.S. patent application Ser. No. 14/256,915, filed Apr. 18, 2014, U.S. patent application Ser. No. 14/630,471, filed Feb. 24, 2015, U.S. patent application Ser. No. 14/809, 109, filed Jul. 24, 2015, and U.S. patent application Ser. No.

14/920,860, filed Oct. 22, 2015, each of which was previously incorporated by reference in its entirety, disclose stimulation devices that may be used in accordance with embodiments of the invention.

Figure 3:
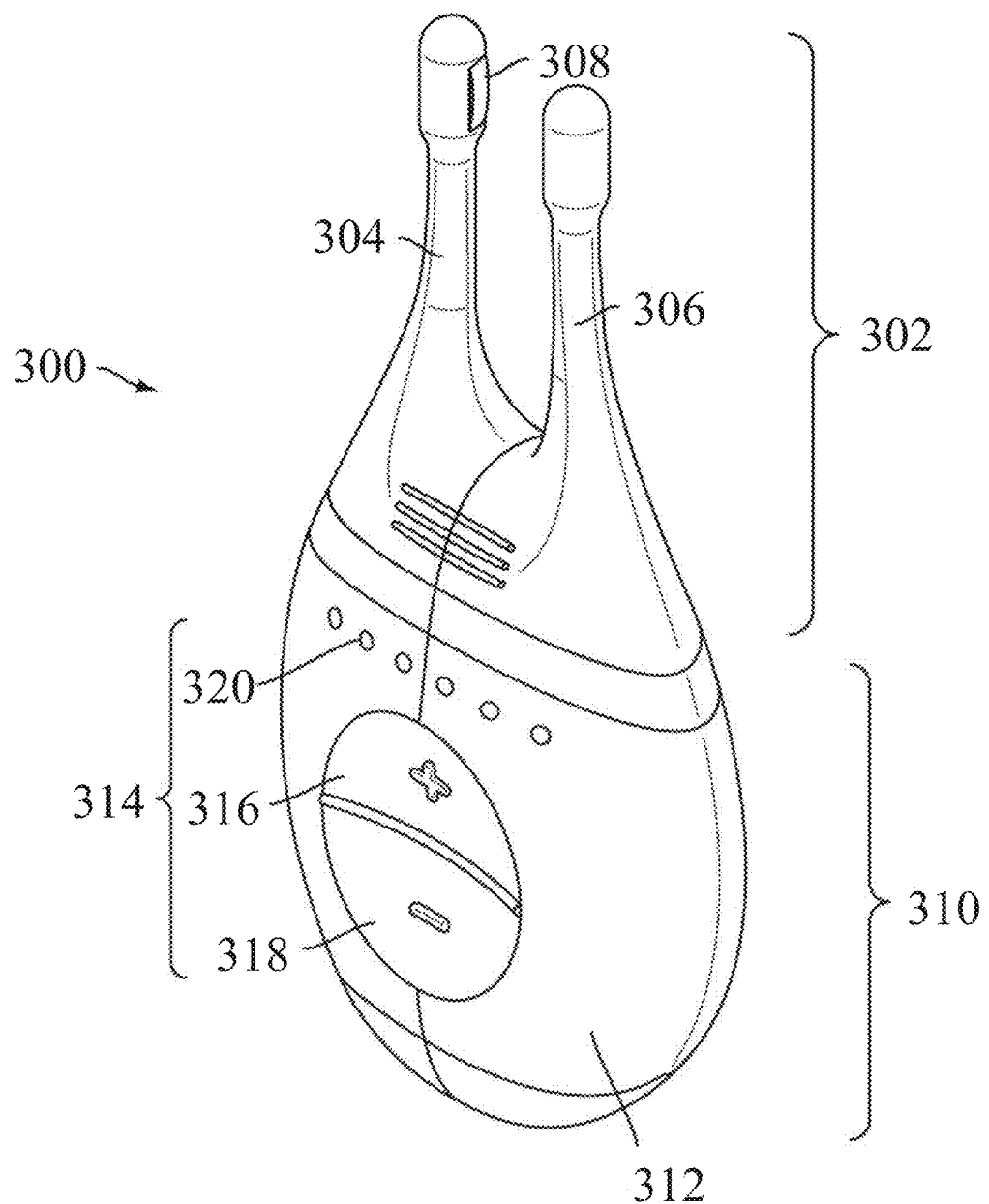
FIG. 3 illustrates a stimulation device utilized in accordance with an embodiment of the invention.

FIG. 3 shows one variation of a stimulation device 300 that may be used in accordance with embodiments of the invention. Stimulation device 300 includes a stimulator probe 302 configured to deliver a stimulus to the patient and having a first nasal insertion prong 304 and a second nasal insertion prong 306, each of which has an electrode 308. The stimulation device 300 also includes a stimulator body 310 configured to generate the stimulus and having a housing 312 and a user interface 314 including indicator lights 320 and buttons 316 and 318. A patient may place the electrodes 308 in contact with nasal tissue (e.g., nasal mucosa adjacent the nasal septum) and deliver a stimulus in accordance with the treatment recommendation.

Additionally or alternatively, stimulation may be manually and/or automatically executed by other suitable stimulation devices. For example, electrical stimulation may be delivered by a microstimulator implant, such as those described in U.S. patent application Ser. No. 13/441,806, filed Apr. 6, 2012 and titled "STIMULATION DEVICES AND METHODS", which is hereby incorporated in its entirety by this reference. Furthermore, other treatment may include ultrasound stimulation (e.g., via ultrasound transducers), chemical stimulation, or any suitable stimulation.

An embodiment of the present invention relates to a computer storage product with a non-transitory computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media, optical media, magneto-optical media and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, JavaScript, or other object-oriented or functional programming languages and development tools. Another embodiment of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A machine, comprising:
a processor; and
a memory connected to the processor, the memory storing instructions executed by the processor to:
determine a first property related to dry eye symptoms of a patient;
determine a second property related to the dry eye symptoms of the patient;
form a dry eye forecast based upon the first property and the second property;
select a treatment recommendation based upon the dry eye forecast; and
supply the treatment recommendation to a device connected to the machine through a computer network,
wherein the first property is a relative humidity (RH) proximate to the patient, the second property is an ambient temperature (T) proximate to the patient, and the dry eye forecast is a value equal to:

$$\begin{cases} 0, & RH*P(T) > 6.28 \\ 100*[6.28 - RH*P(T)]/6.28, & RH*P(T) \leq 6.28 \end{cases}$$

where P(T) is the saturated water vapor pressure at the ambient temperature T.

2. The machine of claim 1, further comprising instructions executed by the processor to determine a third property related to the dry eye symptoms of the patient, wherein the instructions to form the dry eye forecast utilize the first property, the second property, and the third property.

3. The machine of claim 2, wherein the third property is an environmental property proximate to the patient.

4. The machine of claim 3, wherein the third property is a wind speed.

5. The machine of claim 3, wherein the third property is a pollution level.

6. The machine of claim 3, wherein the third property is a pollen count.

7. The machine of claim 3, wherein the third property is condensation data.

8. The machine of claim 3, wherein the third property is an air pressure.

9. The machine of claim 3, wherein the third property is a vapor pressure.

10. The machine of claim 3, wherein the third property is a UV index.

11. The machine of claim 3, wherein the third property is a wind chill.

12. The machine of claim 2, wherein the third property is a patient-specific property.

13. The machine of claim 12, wherein the third property is a schedule of the patient.

14. The machine of claim 12, wherein the third property is a medical condition of the patient.

15. The machine of claim 1, wherein the treatment recommendation includes stimulus delivery to the patient.

16. The machine of claim 15, wherein the treatment recommendation includes a duration of the stimulus delivery.

17. The machine of claim 15, wherein the treatment recommendation includes a time of the stimulus delivery.

18. The machine of claim 15, wherein the treatment recommendation includes a number of periods of the stimulus delivery.

19. The machine of claim 15, wherein the stimulus delivery is an electrical stimulus delivery.

20. The machine of claim 15, wherein the treatment recommendation includes stimulus delivery to a nasal mucosa of the patient.

21. The machine of claim 1, including instructions executed by the processor to supply the treatment recommendation to the device implemented as a computing device.

22. The machine of claim 1, including instructions executed by the processor to supply the treatment recommendation to the device implemented as a stimulation device.

23. A machine, comprising:
a processor; and
a memory connected to the processor, the memory storing instructions executed by the processor to:
determine a first property related to dry eye symptoms of a patient;
determine a second property related to the dry eye symptoms of the patient;
form a dry eye forecast based upon the first property and the second property;
select a treatment recommendation based upon the dry eye forecast; and
supply the treatment recommendation to a device connected to the machine through a computer network,
wherein the first property is a relative humidity (RH) proximate to the patient, the second property is an ambient temperature (T) proximate to the patient, and the dry eye forecast is a value equal to:

$$\begin{cases} 0, & RH*P(T) < 3.768 \\ \dfrac{(100*[6.28-RH*P(T)]/6.28)-40}{60}*100, & RH*P(T) \geq 3.768 \end{cases}$$

where P(T) is the saturated water vapor pressure at the ambient temperature T.

24. The machine of claim 23, further comprising instructions executed by the processor to determine a third property related to the dry eye symptoms of the patient, wherein the instructions to form the dry eye forecast utilize the first property, the second property, and the third property.

25. The machine of claim 24, wherein the third property is an environmental property proximate to the patient.

26. The machine of claim 25, wherein the third property is a wind speed.

27. The machine of claim 25, wherein the third property is a pollution level.

28. The machine of claim 25, wherein the environmental property is a pollen count.

29. The machine of claim 25, wherein the third property is condensation data.

30. The machine of claim 25, wherein the third property is an air pressure.

31. The machine of claim 25, wherein the third property is a vapor pressure.

32. The machine of claim 25, wherein the third property is a UV index.

33. The machine of claim 25, wherein the third property is a wind chill.

34. The machine of claim 24, wherein the third property is a patient-specific property.

35. The machine of claim 34, wherein the third property is a schedule of the patient.

36. The machine of claim 34, wherein the third property is a medical condition of the patient.

37. The machine of claim 23, wherein the treatment recommendation includes stimulus delivery to the patient.

38. The machine of claim 37, wherein the treatment recommendation includes a duration of the stimulus delivery.

39. The machine of claim 37, wherein the treatment recommendation includes a time of the stimulus delivery.

40. The machine of claim 37, wherein the treatment recommendation includes a number of periods of the stimulus delivery.

41. The machine of claim 37, wherein the stimulus delivery is an electrical stimulus delivery.

42. The machine of claim 23, wherein the treatment recommendation includes stimulus delivery to a nasal mucosa of the patient.

43. The machine of claim 23, including instructions executed by the processor to supply the treatment recommendation to the device implemented as a computing device.

44. The machine of claim 23, including instructions executed by the processor to supply the treatment recommendation to the device implemented as a stimulation device.

* * * * *